United States Patent [19]

Detsch

[11] 4,281,990

[45] Aug. 4, 1981

[54] BLADE LOCKING MECHANISM

[76] Inventor: Steven G. Detsch, 4146 Bryan St., Oceanside, Calif. 92054

[21] Appl. No.: 112,740

[22] Filed: Jan. 17, 1980

[51] Int. Cl.³ .............................................. A61C 3/02
[52] U.S. Cl. .................................... 433/144; 30/339; 128/305
[58] Field of Search ....................... 433/144, 146, 147; 128/305; 30/164.9, 339, 337, 320, 329

[56] References Cited

U.S. PATENT DOCUMENTS

| | | | |
|---|---|---|---|
| 445,237 | 1/1891 | Yankauer | 30/339 |
| 2,655,723 | 10/1953 | Steele | 30/339 |
| 3,626,592 | 12/1971 | La Cas | 30/339 |

Primary Examiner—Robert Peshock
Attorney, Agent, or Firm—Michael W. York

[57] ABSTRACT

A blade locking mechanism formed integrally on the end of an elongated instrument handle permitting available slot mounted disposable surgical blades to be attached perpendicular to the axis of the handle service end for use as a knife in applications such as oral surgery. A cleat formed in the service end of the handle projects therefrom in line with the axis of the handle end. The base of the cleat has a rectangular cross-section sized to have a sliding fit within the minimum slot dimension of the disposable blade, and of a length greater than the thickness of the blade. The horns of the cleat lie in a plane perpendicular to the handle service end and are sized to pass easily through the maximum blade slot dimension when in line therewith, but prevent removal of the blade from under the cleat horns when the blade is turned 90° to the axis of the cleat horns and the blade slot is fitted about the cleat base. A locking collar engages threads formed on the handle end adjacent to the cleat, and is movable along the axis of the handle end. The collar locks a disposable blade fitted under the cleat horns in place by clamping it between the collar and the underside of the cleat horns forming a unitized cutting instrument. Excess, base length of the installed disposable blade is trimmed away before use.

5 Claims, 5 Drawing Figures

U.S. Patent    Aug. 4, 1981    4,281,990
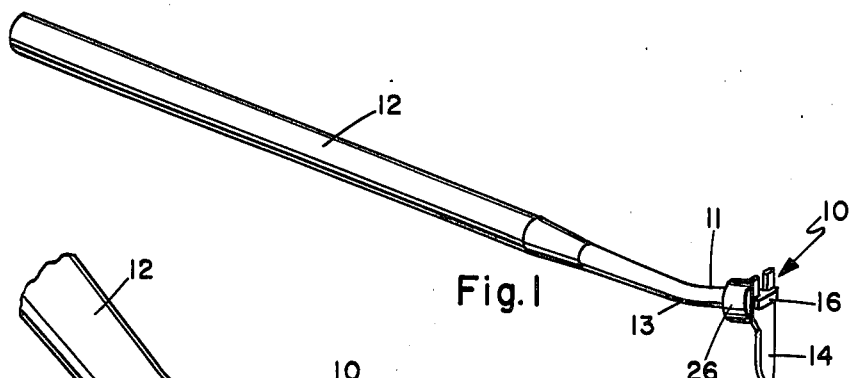
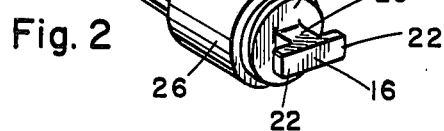
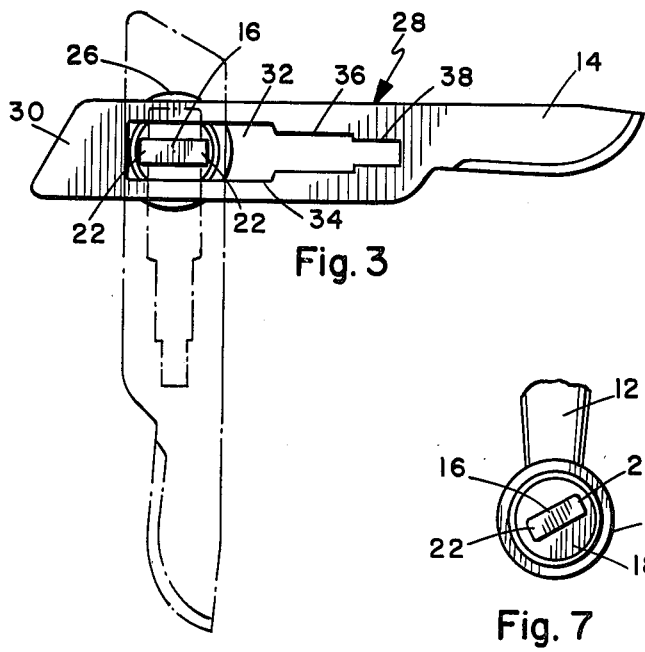
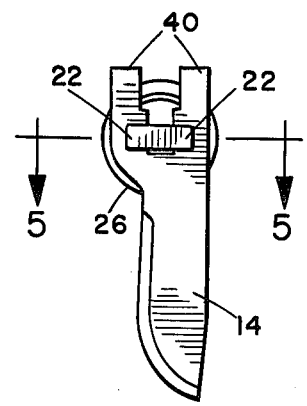
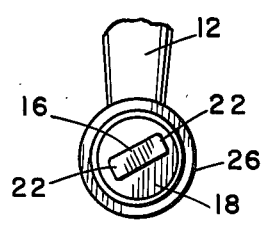
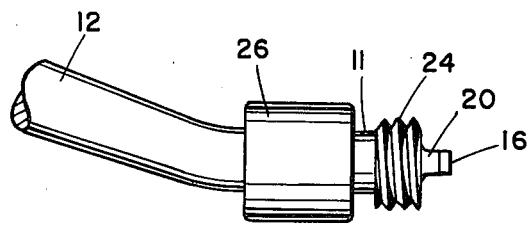
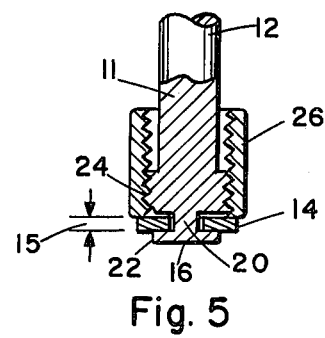

BLADE LOCKING MECHANISM

BACKGROUND OF THE INVENTION

Dental surgery and particularly surgery for the correction or amelioration of periodontal disease is often made difficult and challenging because of the restricted access permitted by the architecture of the mouth. These inherent limitations may prevent or restrict the desired optimal surgical procedures, because of the inability to gain appropriate access to the treatment area with surgical knives having cutting edges of the desired shape, size and approach angulation. It is additionally important to have readily available to the surgeon, a variety of sterile blades of various cutting edge configurations. For best access in locations such as distals of maxillary molars and linguals of mandibular teeth, it is also important to have available an instrument in which the cutting edge of a short blade is positioned perpendicular to the longitudinal axis of the instrument handle, rather than a straight extension of the blade handle.

Several instruments for meeting such surgical requirements are currently available, but each has disadvantages. ORBAN and KIRKLAND knives are manufactured in sets with various blades shapes and approach configurations achieved among the instruments of the set. Such instruments are expensive, and additionally require exacting maintenance. They must be sharpened by a skilled person and otherwise well cared for to insure a sharp true edge and a surgically sterile blade at the time of use. Another approach which overcomes the latter problems is to use disposable surgical blades maintained in sterile packages until mounted upon a handle designed to receive them. The BARD-PARKER, HUFREIDY, and AMERICAN SAFETY RAZOR instruments employ such blades. While providing a variety blade shapes for ready use, the instrument approach angulation in the latter products restricts their use. Characteristically, disposable blades are mounted to their handles by providing the blade base with a rectangular longitudinal slot having sections of varying size which is placed over lugs in the handle and locked in place by sliding the blade into a conforming recess in the handle. As a consequence of these mounting methods, the disposable blade becomes a straight extension of the handle greatly limiting the utility of the instrument in areas of restricted access as compared with a short blade mounted perpendicular to the handle axis.

It is desirable, therefore to provide a surgical blade locking mechanism employable on the service end of an elongated instrument handle which overcomes the cited disadvantages and provides a versatile instrument for oral surgery employing a short disposable blade with an orientation perpendicular to the instrument handle axis.

SUMMARY OF THE INVENTION

The invention relates to a locking mechanism for the end of an instrument handle to permit the ready attachment of available slot mounted disposable surgical blades with an orientation perpendicular to the end of the handle.

An integral cleat is formed at the service end of the instrument with the base section of the cleat projecting from such end in the plane of the instrument handle. The base of the cleat is of rectangular cross section and sized to permit a sliding fit into the smallest section of the blade slot to prevent rotation of a mounted blade. The length of the cleat base is longer than the thickness of a disposable blade. The horns of the cleat are of equal length and rectangular in cross section and lie in a plane parallel to the end face of the handle. The combined length of the horns is not greater than the periphery of the handle end. In one embodiment, the horns are perpendicular to the plane of the instrument handle. The cleat horns are sized such that they may pass easily through larger slot sections of a disposable blade when in line therewith, but prevent withdrawal of a blade from under the horns when the blade is turned ninety degrees to the axis of the cleat horns and the minimum slot section is fitted about the base section of the cleat. A locking collar with internal threads engages corresponding threads formed at the end of the handle adjacent to the cleat base. When a disposable blade is fitted on the cleat under its horns, movement of the locking collar toward the cleat locks the blade in place by clamping it between the collar and underside of the cleat horns. When secured in the locking head, the excess blade mounting base length of the blade is trimmed off to provide a short cutting blade mounted perpendicular to the axis of the instrument.

In an alternate embodiment the cleat is formed with its horn axis at an acute angle to the plane of the instrument handle. Such an orientation results in the cutting edge of an installed blade being at an angle to the plane of the handle which in conjunction with any handle terminal offset further facilitates access to particular areas of the mouth.

The primary object of the invention is to provide a new and improved blade locking mechanism for installation of disposable surgical blades on the end of an instrument handle. The mechanism secures the blade to the instrument with an orientation perpendicular to the end of the instrument handle, thus improving approach angulation for oral surgery procedures in constricted areas. The mechanism permits the use of various cutting edge configurations available with disposable blades and avoids the necessity of maintaining in readiness a sharpened set of sterile dental instruments with a consequent savings in cost and time. The instrument handle and locking mechanism are easily produced and are inexpensive. The configuration of the locking mechansim permits easy and rapid installation and change of available disposable blades of differing shapes with use of a single handle. These together with other objects and advantages will become apparent in considering the details of construction and operation of the blade locking mechanism as they are more fully described. Reference will be made to the accompanying drawings wherein like numerals refer to like parts throughout, and in which:

FIG. 1 is a perspective view of the complete instrument with a blade attached.

FIG. 2 is an enlarged perspective view of the blade locking mechanism.

FIG. 3 is an end view of the mechanism showing the blade attaching method.

FIG. 4 is an end view showing the blade base trimmed away and the cutting edge locked in place.

FIG. 5 is a sectional view taken on line 5—5 of FIG. 4.

FIG. 6 is a side elevational view of the locking mechanism with the locking collar retracted.

FIG. 7 is an end view showing an optional angular offset for the blade locking cleat.

DETAILED DESCRIPTION OF THE DRAWINGS

FIG. 1 shows the blade locking mechanism 10 formed at the service end 11 of an elongated instrument handle 12. Locking mechanism 10 and handle 12 are formed from metal or plastic capable of withstanding autoclaving, thermal, or chemical sterilization. The working portion of a disposable blade 14 is shown installed in locking mechanism 10 ready for use. Handle 12 is shown with a curved or offset section 13 near its working end 11. Different angular offset may be provided in the instrument handle 12 to facilitate further blade entry in particular surgical areas. The design and construction of the locking mechanism 10 is depicted in FIGS. 2, 5 and 6. FIG. 2 shows cleat 16 projecting from the center of end surface 18 of handle 12. Cleat 16 is formed as a solid member integral with the service end 11 of handle 12. Cleat base 20 is rectangular in cross section and forms an extension of handle 12. The axis of rectangularly shaped cleat horns 22 is parallel to handle end surface 18 and lies in a plane perpendicular to the plane of instrument handle 12. Cleat horns 22 project from base section 20 and are of equal length. Horns 22 do not extend beyond the handle end surface 18.

As shown in FIGS. 5 and 6, locking threads 24 are formed at the service end 11 of handle 12 adjacent to cleat 16, and locking collar 26 is threadable thereon. Collar 26 may be removed from handle 12 by threading it toward cleat 16, or allowed to fit loosely about the service end 11 of handle 12 if it is backed off the threads 24 in the opposite direction.

A typical disposable blade 28 is shown in FIG. 3. Such blades have a base section 30 of standardize configuration and a knife section 14 which is available in varying cutting edge shapes and sizes. Blade base section 30 is provided with a rectangular mounting slot 32 consisting of in-line sections 34, 36 and 38 of diminishing size. The smallest slot section 38 has dimensions such that the cleat base 20 has a snug but sliding fit into its opening so as to hold and prevent rotation of a mounted blade. When blade slot 32 is in line with cleat horns 22, the latter may be passed easily through blade mounting slot 32, as indicated in the full line blade representation of FIG. 3. When the disposable blade 28 is turned 90° under cleat horns 22, as shown in the broken line blade representation of FIG. 3, the span of cleat horns 22 prevents the subsequent removal of blade 28 from the under cleat horns 22, but allows the movement of cleat base 20 within the slot sections 34, 36 and 38 until it is seated in slot section 38. Disposable blade thickness is indicated as dimension 15 in FIG. 5.

FIG. 7 shows an embodiment of the locking mechanism 10 in which locking cleat 16 is formed with the axis of cleat horns 22 at an acute angle to the plane of the instrument handle 12 rather than being perpendicular thereto. Variations in such angular placement of cleat 16, in combination with different offset sections 13 of handle 12, can provide an instrument and blade locking mechanism arrangement of great versatility in aiding the surgeons approach for particular surgical procedures.

OPERATION

To use the instrument handle 12 equipped with blade locking mechanism 10, locking collar 26 is backed away from cleat 16 on threaded section 24 to permit a blade 28 to be fitted under the horns 22 of the cleat 16. Slot 32 of disposable blade 28 is then aligned with the axis of cleat horns 22 and the horns are passed through slot 32 at its maximum slot section 34. Blade 28 is then turned 90° under horns 22, and cleat base 20 is fitted into the minimum size section 38 of blade slot 32. With blade 28 thus positioned, its further rotation is prevented. Locking collar 26 is then advanced along threads 24 toward cleat 16 until the blade is firmly clamped between locking collar 26 and the flat underside of horns 22 of cleat 16. Base section 30 of blade 28 is then trimmed away with an appropriate tool at portions 40 as shown in FIG. 4, to provide a short blade section 14 mounted perpendicular to the service end 11 of handle 12.

Having described my invention, I now claim:

1. A blade locking mechanism for the end of a surgical instrument handle for attachment of slot mountable surgical blades to the service end of said surgical instrument handle comprising means located on the service end of said surgical instrument for mounting said surgical blades perpendicular to the service end of said surgical instrument, said mounting means comprising a cleat integrally formed in said handle service end and projecting from said handle service end surface for attaching said blade to said handle service end, said cleat comprising a base section and cleat horns formed at the projecting end of the base section with the axis of the horns lying in a plane perpendicular to said handle service end, said cleat horns being sized and shaped to pass through the slot in said blade when in line therewith but preventing withdrawal of said cleat horns from the slot of said blade by contacting the blade adjacent the slot in the slot mountable surgical blade when said blade is turned 90 degrees to said cleat horns, a threaded section on said handle service end adjacent to said cleat and a locking collar threadable on the threaded section to clamp a mounted blade between the locking collar and the underside of said cleat horns.

2. A blade locking mechanism as recited in claim 1 wherein:
the cleat base section is rectangular in cross section preventing rotation of said blade when the base section is fitted into the minimim slot dimension of said blade,
the cleat horns are rectangular in cross section providing for the firm seating of said blade against the cleat horns.

3. A blade locking mechanism as recited in cliam 1 wherein:
the cleat horns are of equal length, and do not extend beyond the periphery of said handle service end.

4. A blade locking mechanism as recited in claim 1 wherein:
the axis of the horns of the cleat lies at an acute angle to the plane of said instrument handle.

5. A blade locking mechanism as recited in claim 1 wherein
the locking mechanism and said instrument handle are formed from materials capable of withstanding autoclaving, thermal, or chemical sterilization.

* * * * *